United States Patent
Vuillermoz et al.

(10) Patent No.: US 7,223,978 B2
(45) Date of Patent: May 29, 2007

(54) METHOD FOR MEASURING GASEOUS SPECIES BY DERIVATION

(75) Inventors: Jean-Claude Vuillermoz, Versailles (FR); Jacky Laurent, Saint-Cyr L'Ecole (FR); Savine Bockel-Macal, Villebon-sur-Yvette (FR); Fabien Januard, Versailles (FR); Bruno Allemand, Dunkerque (FR)

(73) Assignee: L'Air Liquide, Société Anonyme à Directoire et Conseil de Surveillance pour l'Étude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 10/568,698

(22) PCT Filed: Aug. 31, 2004

(86) PCT No.: PCT/FR2004/050401

§ 371 (c)(1), (2), (4) Date: Feb. 17, 2006

(87) PCT Pub. No.: WO2005/024398

PCT Pub. Date: Mar. 17, 2005

(65) Prior Publication Data

US 2006/0202123 A1 Sep. 14, 2006

(30) Foreign Application Priority Data

Sep. 1, 2003 (FR) .................................. 03 50484
Jul. 29, 2004 (FR) .................................. 04 51698

(51) Int. Cl.
*G01N 1/22* (2006.01)

(52) U.S. Cl. ..................................................... 250/343
(58) Field of Classification Search ................. 250/343
See application file for complete search history.

(56) References Cited

U.S. PATENT DOCUMENTS 3,564,237 A   2/1971   Takeuchi et al.
5,344,122 A   9/1994   Vuillermoz et al.

(Continued)

FOREIGN PATENT DOCUMENTS

CA         2 158 516         1/1997

(Continued)

OTHER PUBLICATIONS

International Search Report for PCT/FR2004/050401.

*Primary Examiner*—David Porta
*Assistant Examiner*—Mark R. Gaworecki
(74) *Attorney, Agent, or Firm*—Christopher J. Cronin

(57) ABSTRACT

The invention relates to a method for measuring the quantity of chemical species contained in a high-temperature gas, and especially the quantity of CO and/or $CO_2$ contained in a gas emitted from a metal treating furnace, especially a light-arc furnace (EAF) or a converter (BOF). According to the invention, part of the gas to be analysed is extracted, the temperature of said gas is reduced to at least 300° C., preferably to a temperature that is lower than or equal to 200° C., in such a way as to obtain a at a temperature between 300° C., preferably 200° C., and the ambient temperature, and at least the quantity of CO and/or $CO_2$ said gas is then measured by means of the coherent light signal which is emitted by a laser diode through the gas and is retrieved on emergence from the gas.

6 Claims, 4 Drawing Sheets

U.S. PATENT DOCUMENTS

Figure 1:
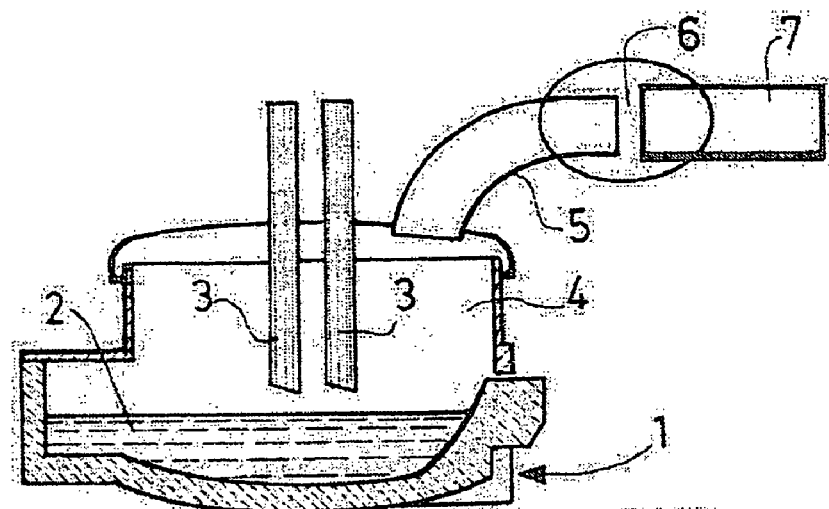

| | | | |
|---|---|---|---|
| 5,490,429 A * | 2/1996 | Jarolics | 73/863.83 |
| 5,984,998 A | 11/1999 | Ottesen et al. | |
| 7,022,992 B2 * | 4/2006 | Grant et al. | 250/339.13 |
| 2003/0132389 A1 * | 7/2003 | Von Drasek et al. | 250/343 |
| 2003/0160174 A1 * | 8/2003 | Grant et al. | 250/339.13 |
| 2004/0207851 A1 | 10/2004 | Dietrich | |

FOREIGN PATENT DOCUMENTS

| | | |
|---|---|---|
| WO | WO 99 26058 | 5/1999 |
| WO | WO 01 33200 | 5/2001 |
| WO | WO 02 090943 | 11/2002 |
| WO | WO 03 060480 | 7/2003 |

* cited by examiner

METHOD FOR MEASURING GASEOUS SPECIES BY DERIVATION

The present invention relates to a method and to a device for measuring the quantity of chemical species contained in a high-temperature gas and especially the quantity of CO and/or $CO_2$ contained in a gas output by a metal treatment furnace, and especially an electric arc furnace (EAF) or a basic oxygen furnace (BOF) or converter.

The invention is aimed more particularly at providing a solution for the continuous chemical analysis of the flue gases, collectively called off-gas, from an electric arc furnace, said off-gas being at high temperature (around 1800° C.) and laden with dust (100 to 200 g/Nm$^3$).

By continuously analyzing the off-gas of a furnace it is possible to obtain information about the treatment process: material and energy balance, state of the chemical reactions inside the furnace, etc. The systems for analyzing the composition of the off-gas, especially that output by an electric arc furnace, must withstand a particularly hostile environment, firstly because of the high temperature of the off-gas (around 1800° C.) and secondly because of the high dust concentration (100 to 200 g/Nm$^3$), this dust also being very fine (down to 1 micron in size).

A first method, developed by the Applicant and known by the commercial name ALARC AS (and described for example in U.S. Pat. No. 5,344,122) consists in taking samples of off-gas and analyzing these samples: a water-cooled sampling probe is placed in the gap that exists between the outlet of the furnace and the gas exhaust duct of the furnace so as to withdraw a sample and take it into a region where the dilution with ambient air is minimal. The sample thus has a composition representative of the chemical composition inside the furnace. The sample is filtered and then conveyed via a heated line (heated so as to prevent the temperature dropping below the dew point of water, and therefore preventing this water from condensing) to a dryer and then to the various analyzers used: infrared analyzers for measuring the carbon monoxide and carbon dioxide concentrations, thermal conductivity analyzers for measuring the hydrogen concentration, and electrochemical or paramagnetic cells for measuring the oxygen concentration.

However, such a system has a number of drawbacks:

response time: to prevent the filters and dryers from clogging up too rapidly, the withdrawal rate is low. Since the analyzers must be located in areas where the temperature conditions are stable (environmentally controlled box or room), the analyzers are often located relatively far from the sampling point, resulting in a large dead volume. Associated with a low rate, the response time of the analytical system is long, ranging from around 30 seconds to 3 minutes; and maintenance: with the large quantity of dust in the off-gas, the filters are rapidly saturated therewith. Likewise, inside the sampling probe, the mixture withdrawn, consisting of dust and locally condensed water, rapidly forms a sealed plug. Unclogging cycles are provided so as to unclog this orifice with compressed air or nitrogen, but the long-term operation requires frequent maintenance (to change filters, to clean or replace the sampling probes, etc.) which, depending on the type of installation, is restrictive to a greater or lesser extent.

Another known method consists in using a coherent light beam emitted by a laser source, and especially a diode laser whose wavelength can vary within a certain wavelength range (for example a TDL or tunable diode laser).

The measurement of the composition of a gas by spectroscopy, especially using laser radiation, is based on the property of gas molecules to absorb radiation at characteristic wavelengths (defined by the absorption spectrum specific to each molecule of the gas).

U.S. Pat. No. 5,984,998 (or WO-A-99/26058) and CA-A-2158516 disclose a laser radiation system for measuring the absorption spectrum of the off-gas in the gap in order to measure the CO and $O_2$ concentrations of this off-gas. However, certain systems use a wavelength range lying in the middle of the wavelength range corresponding to the infrared (also called the "mid-infrared"). This has the drawback of requiring cryogenically cooled lasers—apart from their high cost, these instruments lack flexibility and cannot be easily transported.

WO-A-01/33200 discloses a system for analyzing the off-gas using a TDL operating in the wavelength range corresponding to the infrared near the visible (called the "near-infrared") allowing measurements by laser absorption spectroscopy of the various constituents: CO, $CO_2$, $O_2$, $H_2O$, etc. One of the advantages of this type of instrument and method is that low-power diode lasers are used, which emit radiation in wavelengths close to those intended in general for telecommunication, and conveyed in optical fibers, said fibers, tailored to such wavelengths, being available to bring, without appreciable loss, the radiation output by the diode laser right to the off-gas duct or gap. The radiation then passes through the off-gas duct or gap, is partly absorbed by the molecules that it is desired to analyze, and is received by a receiver.

This particularly effective system does, however, under certain circumstances, prove to be difficult to use when the off-gas to be analyzed has a high dust content: for example, it is very quickly observed that, during operation of an electric arc furnace, the light signal received by the receiver located at the gap becomes, after a few minutes, too low to be interpreted. Thus, application WO-A-01/033200 proposed placing a screen over at least part of the width of the off-gas duct, acting as a deflector and preventing the stream of dust-laden off-gas from attenuating the light radiation too greatly. The drawback of such a system is the insertion of a fitted part that is permanently present in the off-gas duct where the temperature is around 1500° C. WO-A-02/090943 describes a similar solution, which has the same drawbacks.

The problems inherent in a measurement based on a light beam emitted by a diode laser passing through the off-gas duct at the gap of an electric furnace may be summarized thus:

loss of signal: when the concentration of dust particles becomes too high, their scattering (the particles are approximately spherical, with a diameter of the order of the wavelength of the laser) attenuates the transmitted intensity of the laser, and the recovered signal has an amplitude such that the signal/noise ratio is too low for this signal to be exploitable;

species measured: in the near-infrared and at temperatures around 1500° C., not all the lines of the chemical species it is desired to measure are exploitable. This is because, in order to be able to determine a species accurately, without interference from another species, the absorption line that characterizes this species must be sufficiently separate from the characteristic lines of the other chemical species likely to be present in the off-gas. The variation in temperature affects the distribution and the intensity of the absorption peaks: the wavelengths used at room temperature for measuring a given gas can in general no longer be used at other temperatures. For example, for wavelengths in the near-infrared, the absorption lines characteristic of $CO_2$ can no longer be measured accurately above about 200° C. The $CO_2$ concentration therefore cannot be measured directly in the gap, where the temperatures reach 1400 to 2000° C. using laser radiation in the near-infrared. In the case of an oxygen concentration measurement for example, this problem is aggravated by the low emission power of commercially available diode lasers in the range of wavelengths in question: with a high dust content, the transmitted power is too low to provide a reliable signal; and measurement accuracy: two phenomena upset the accuracy of a direct measurement in the gap. Firstly, the presence of dilution air, which is entrained by the hot gas via this opening and which cools said gas, while causing combustion of the carbon monoxide leaving the furnace. Knowing that the concentration measurement given by the diode laser is the absorption averaged over the path taken by the radiation, the composition of the dilution air and its effects have an effect on this calculation. The measurement is therefore less representative of the atmosphere in the furnace. Secondly, the temperature conditions also disturb the accuracy of the measurement: at high temperature, the water absorption lines are omnipresent and greatly confuse the measurement and increase the uncertainty.

According to a first aspect, the invention aims to measure, in particular and preferably, the CO and $CO_2$ concentrations, and optionally the $O_2$ and $H_2O$ concentrations, in the off-gas output from a furnace with a response time of less than 10 seconds, usually around 5 seconds, making it possible in particular to control the furnace in real time by overcoming the aforementioned drawbacks.

Another aspect of the invention relates to the blocking of the gas sampling lines due to dust in the off-gas, as explained above.

EP-A-0462898 teaches a method of taking a sample and analyzing it, using a water-cooled sampling probe placed in the gas exhaust duct of the furnace so as to draw off a sample into a region where the dilution with air does not corrupt the measurement. The sample thus has a composition representative of the chemical composition inside the furnace. The sample is filtered and then conveyed via a heated line (heated so as to prevent the temperature falling below the dew point of water) as far as means for extracting this water vapor, and then to the analyzers. These are those commonly used, namely infrared analyzers for carbon oxides, thermal conductivity analyzers for hydrogen, and electrochemical or paramagnetic cells for oxygen.

The problems inherent in a sampling system followed by conventional analyzers are the following:

response time: to prevent the filters and dryers from clogging up too rapidly, the withdrawal rate is low. Since the analyzers must be located in areas where the temperature conditions are stable (environmentally controlled box or room), the analysis bay is often located relatively far from the sampling point, resulting in a large dead volume. With the low rate, the response time of the analytical system is considerable (between 30 seconds and 3 minutes); and maintenance: with the large quantity of dust in the off-gas, the filters are relatively rapidly saturated therewith. Likewise, inside the sampling probe, the mixture withdrawn, consisting of dust and locally condensed water, rapidly forms a plug that blocks off the gas passage. Unclogging cycles are provided, by blowing compressed air or nitrogen, but the long-term operation requires frequent maintenance (to change filters, to clean or replace the sampling probes, etc.) which, depending on the type of installation, is restrictive to a greater or lesser extent.

The method according to the invention is characterized in that a portion of the gas to be analyzed is taken off, its temperature is lowered down to less than 300° C., preferably down to a temperature of 200° C. or below, so as to obtain a gas with a temperature between 300° C., preferably 200° C., and room temperature, and then at least the quantity of CO and/or $CO_2$ present in this gas is measured by means of the coherent light signal that is emitted by a diode laser through said gas and recovered upon emerging from said gas.

The coherent light beam may be reflected in a known manner using a mirror and sent back through the gas to be analyzed, or else recovered directly upon emerging from the gas. It is conveyed via an optical fiber and/or converted directly into an electrical signal, in a manner known per se.

According to the invention it is thus possible to measure a single species, whatever the species, but also several species and especially a species chosen from CO and/or $CO_2$ and/or $O_2$ and/or $H_2O$. It is also possible to measure the temperature of the gas in the gap directly using a diode laser by measuring the adsorption of two lines of any one species within the range of wavelengths continually scanned within the wavelength range of the TDL, or else by using a temperature sensor, in a manner known per se, preferably with the aid of a diode laser emitting in the near-infrared, preferably including the 1581 nanometer wavelength.

According to another aspect of the invention, the aim of the latter is to provide an effective system for automatically unclogging the sampling probes for taking dust-laden gas samples, and especially one that is applicable to the system described in the abovementioned patent application. Combined with a pneumatic unclogging device is a moving part that removes, during each unclogging operation, the dust that has built up in the probe. This type of unclogging operation gets round the problem of the accretion of dust and water that attaches to the walls of the probe and that is not removed by blasting with compressed air. The maintenance operations carried out on the probe are therefore greatly reduced and sampling is available throughout the heat.

The essential part of these unclogging means consists of a rod with at least two fins that can be rotated, for example by means of an air cylinder, so as to sweep substantially the entire inner wall of the probe in which these fins move. The rotation is accompanied by a blast of compressed air (either at the same time or afterwards) which expels the dust accretions on the wall.

Preferably, in this unclogging system (in order to draw off the minimum amount of dust while still taking a sample from a region representative of the atmosphere in the furnace), the end of the sampling probe will be beveled and the probe placed so as to draw off, preferably countercurrently, the flow of off-gas. The orifice via which the gas is conveyed is thus protected from being directly splashed, for example with slag, thereby preventing this end from becoming blocked.

More particularly, this other aspect of the invention relates to a system for unclogging a probe of axial symmetry for taking samples from a gas stream containing impurities.

The system according to this aspect of the invention is characterized in that it comprises a part that can move about the axis of symmetry of the probe and can remove the impurities that have built up on the internal wall of said probe by relative rotation of the part and/or of the probe about the axis.

According to a preferred embodiment, this system is characterized in that it includes additional pneumatic unclogging means using compressed air.

Figure 2:
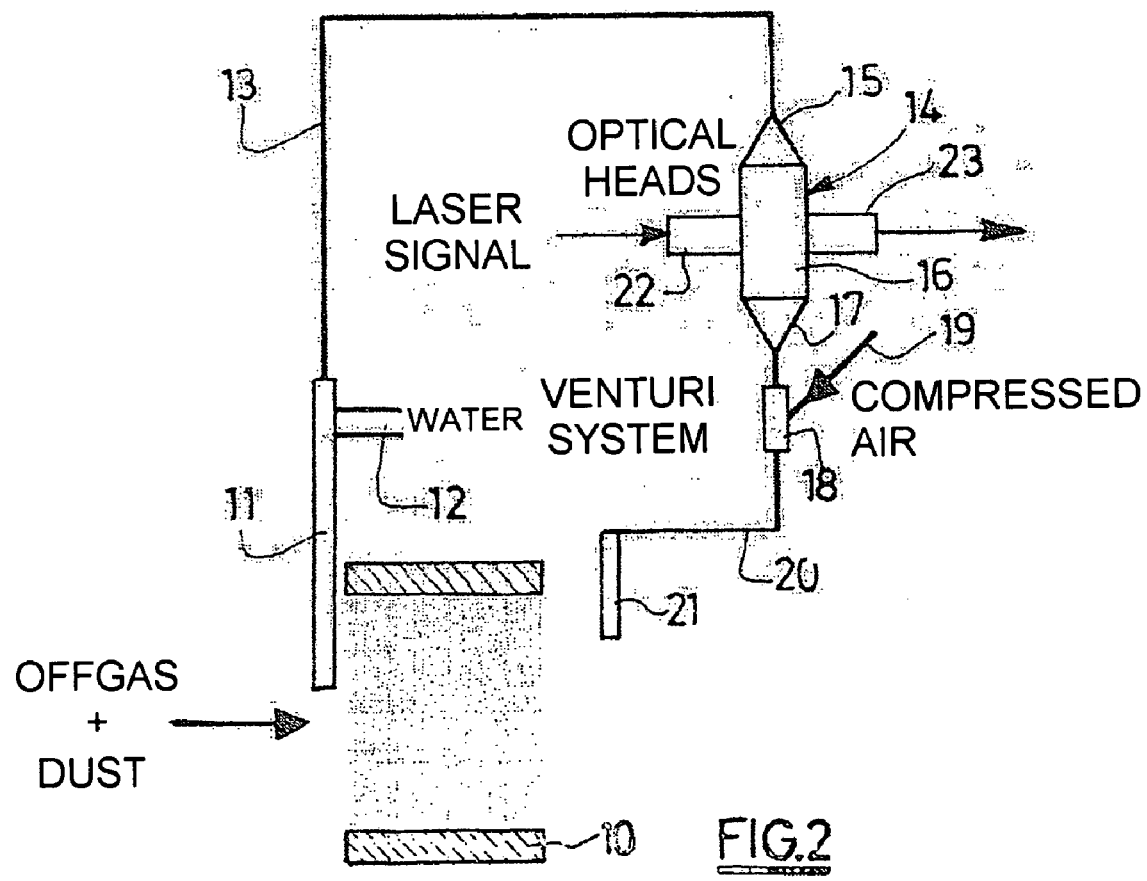
Figure 3:
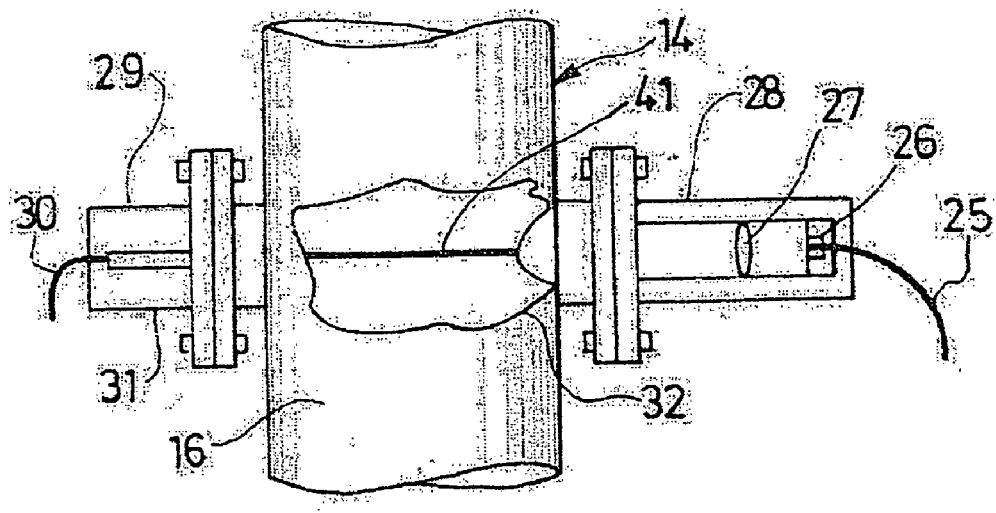
Figure 4:
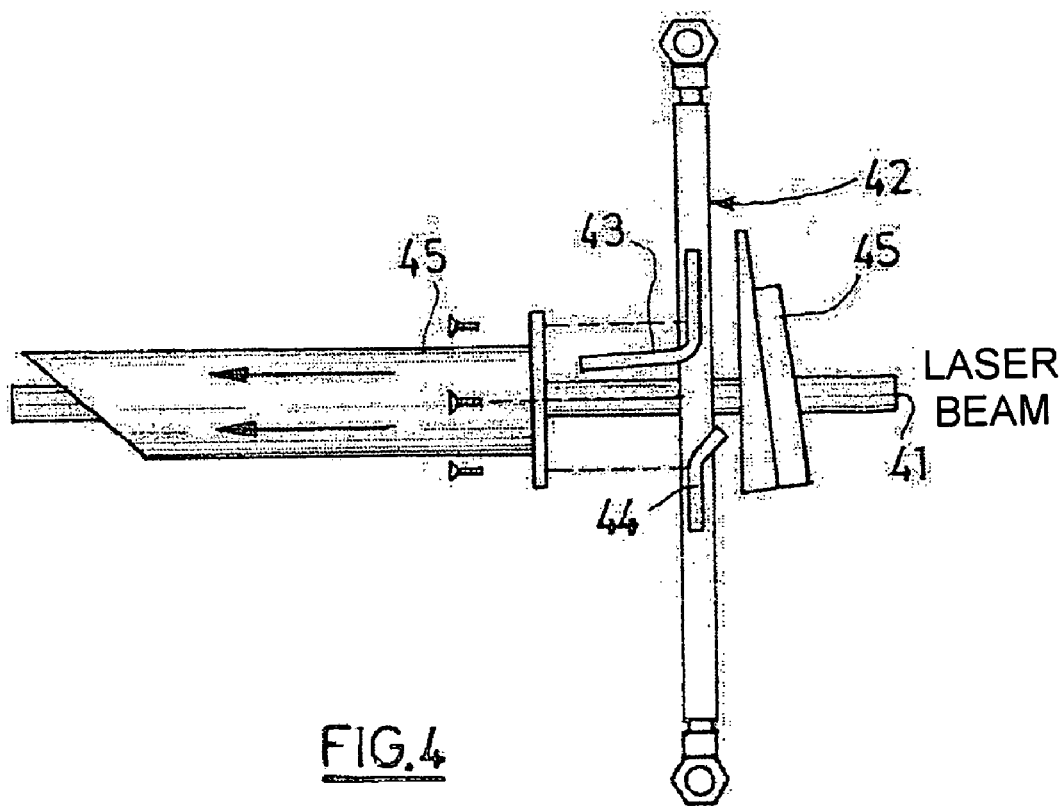
Figure 5:
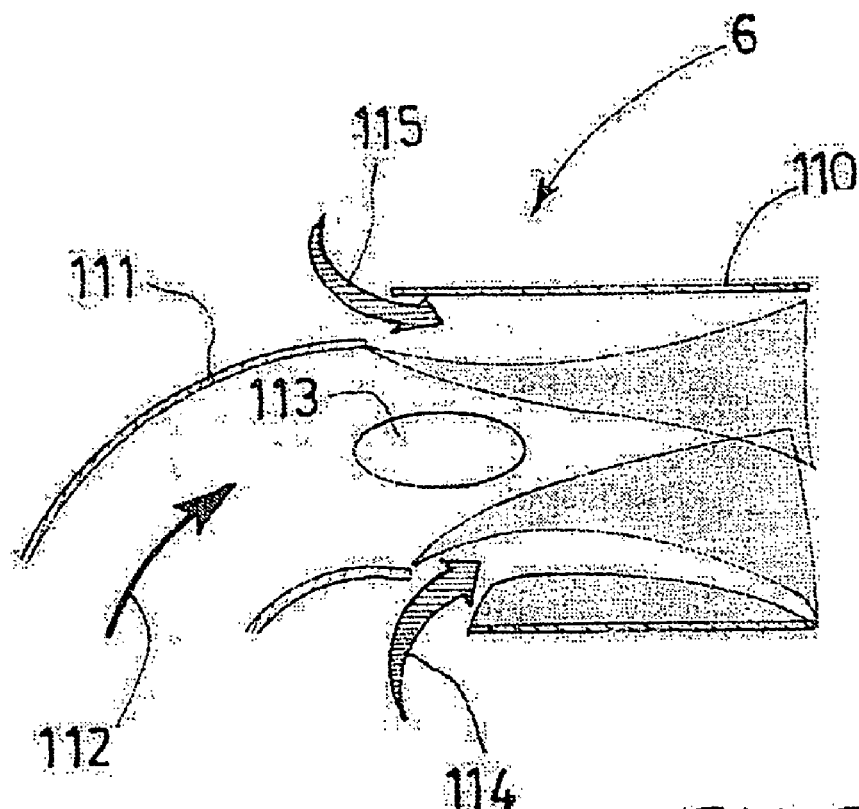
Figure 6:
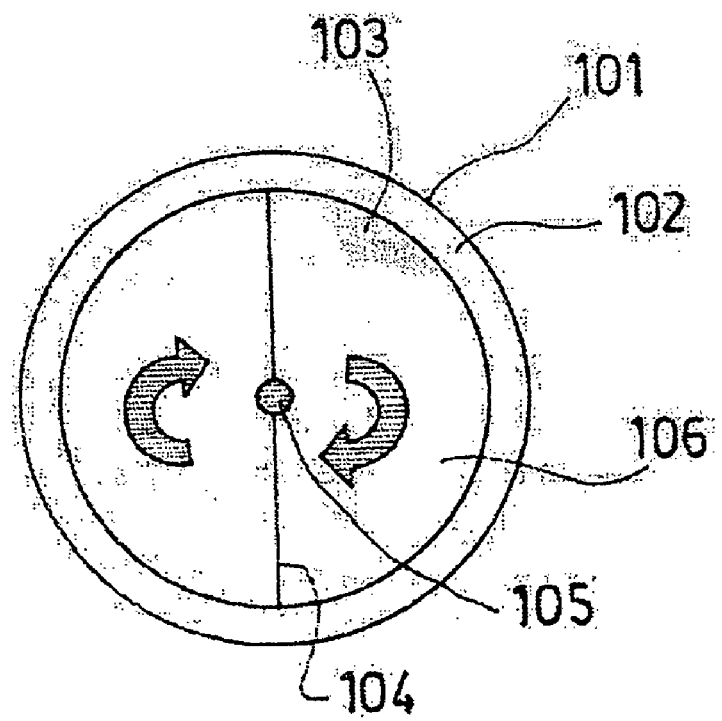
Figure 7:
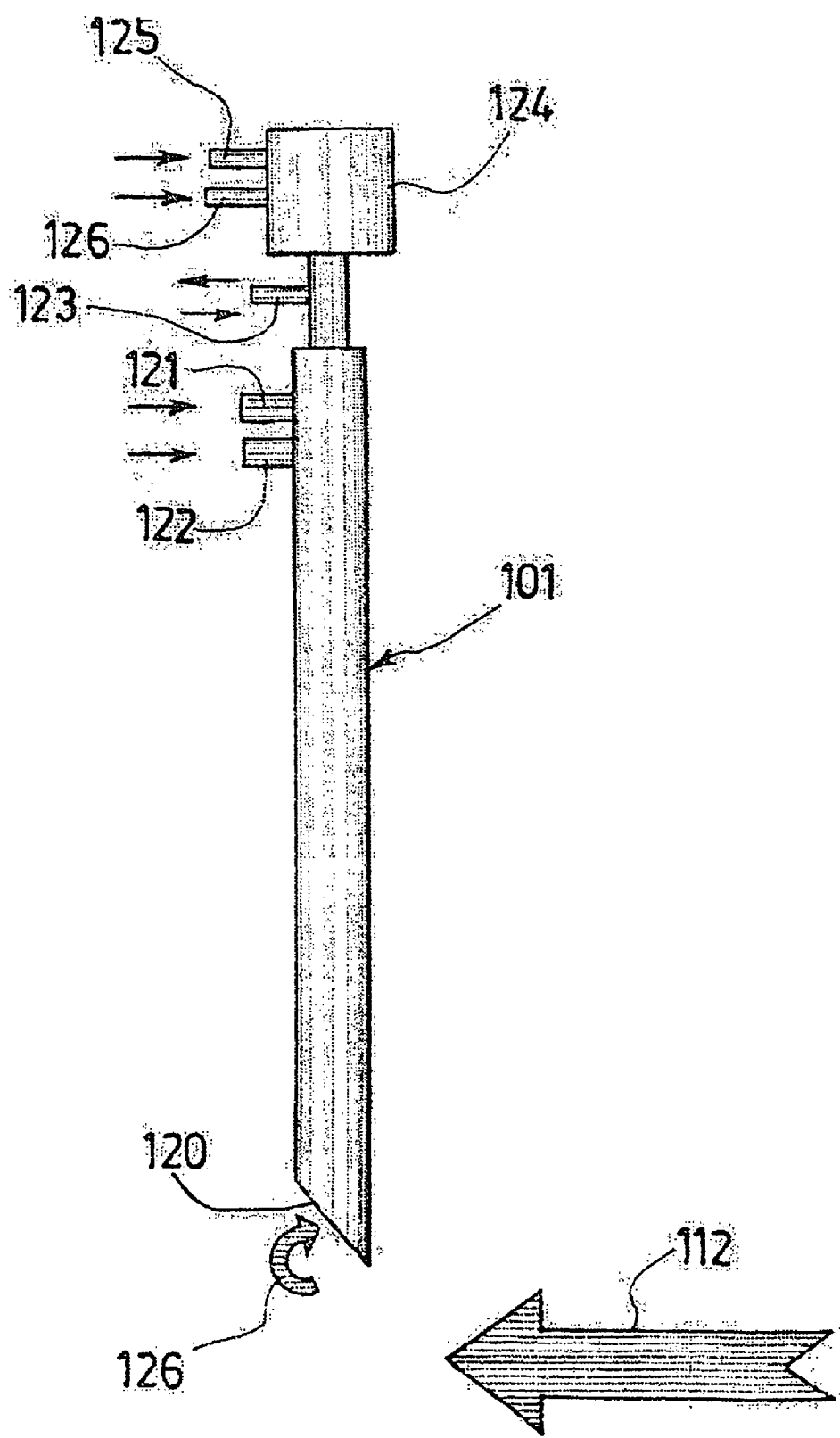

The invention will be more clearly understood with the aid of the following exemplary embodiments, given by way of nonlimiting example, in conjunction with the figures which show:

FIG. 1, a schematic view of an electric furnace of the EAF type,

FIG. 2, a schematic view of the method and device for implementing the invention;

FIG. 3, a detailed view of the system for measurement in the off-gas, the temperature of which has been lowered;

FIG. 4, a schematic view of the system for cleaning the optics;

FIG. 5, a detail of FIG. 1;

FIG. 6, a diagram showing the principle according to the invention of the unclogging of the sampling probe; and FIG. 7, a view of the sampling probe according to the invention.

FIG. 1 is a diagram of an electric arc furnace EAF 1 in the lower part of which lies the molten metal 2, near the electrodes 3 that are surrounded by an atmosphere 4 of off-gas extracted via the duct 5. To allow the roof of the furnace to be maneuvered in various ways, the duct 5 is separated from the duct 7, which extends it, by a gap 6 between the two. It is within this gap that the sampling system of FIG. 2 is placed.

In FIG. 2, a gas sample is taken off from the duct 10 at the outlet of the furnace, from a gas stream representative of the atmosphere in the furnace, but not contaminated with dilution air, by means of a sampling probe 11 cooled by water 12, with a withdrawal rate higher than that of the withdrawal probes of the prior art. The probe 11 has a larger diameter and may optionally contain a mechanical unclogging system. The gas taken off by the probe 11 at a temperature of about 1500° C. is cooled by flowing through the cooled probe 11 into the line 13 and into the chamber 14 on either side of which the optical heads of the diode laser are attached. The entire system—probe 11, line 13 and chamber 14—has a geometry (diameter, length) that depends on the material used and on its capacity for heat exchange with the cooling (water), in such a way that the temperature of the off-gas, when it enters the chamber 14, does not exceed 300° C., preferably 200° C. The distance between the emitting optic 22 and the receiving optic 23 is reduced to a few tens of centimeters (from 1 to 100 cm, preferably 5 to 50 cm and ideally 10 to 15 cm, representing the diameter of the chamber 14). The off-gas is withdrawn, for example, by a Venturi system 18 supplied with a fluid, preferably compressed air 19 de-oiled beforehand in order to prevent dust accretion downstream of the blowing. The analyzed gas sample is discharged via the line 20 and the pipe 21 into the duct 10.

The sampling and analysis system described in the case of an electric arc furnace can be applied to any furnace off-gas exhaust system (without being limited to an electric furnace).

FIG. 3 shows a detail of the chamber 14 of FIG. 2 and of the optics for the diode laser system used. The diode laser emitting coherent laser radiation is not shown in FIG. 3: the radiation arrives via the optical fiber 30 at its end 31, which sends the radiation onto the lens 27, inside the sleeve 28 then to the inside 16 of the chamber 14 and then inside the sleeve 28; the parallel beam 32 is focused by the lens 27 onto the receiver 26 and the signal is sent into the fiber 25.

FIG. 4 is an exploded view of a system for cleaning the optics and of the ducts placed at the optics so as to ensure they are kept clean. A line for supplying inert gas, for example nitrogen, argon, helium or any species whose presence is controlled and therefore will not disturb the measurement to be carried out, includes an injection arm 44 for injecting the inert (or other) gas into the optic carried by the support 45 and through which the laser beam 41 passes, while another arm 43 prevents the cylindrical tube placed around the beam 41 to protect it from dust from being blocked. This cleaning system may if necessary be applied in the chamber 14, but also directly in the gap 6 (FIG. 1) or in the duct 10 (FIG. 2), in which case the measurement would be carried out directly in the gap according to the systems of the prior art, with a distance between the ends of the two tubes 45 on either side of the duct 10 (defining a "free" path for the laser beam in the dust-laden atmosphere of the duct 10) which must in no case be greater than 30 cm in order to ensure lasting operation of the system. The cleaning gas flow rate is generally constant during a heat and increased between heats in order to expel any dust.

The laser signal may either be conveyed near the furnace by means of an optical fiber, while the optical signal received by the optical sensor 23 after having passed through the off-gas is converted into an electrical signal by this sensor and transmitted via a coaxial cable to the central control unit, where it is reconverted into an optical signal and then transmitted via an optical fiber to the central control unit. The optical heads 22, 23, which are placed on either side of the analysis chamber, easily withstand the temperature differences, and the accumulation of dust and splashes. All the emission electronics (diode laser, etc.) and signal processing electronics are placed at a substantial distance (usually around 30 meters) from the furnace, without this affecting the response time.

If desired, it is also possible to produce the laser signal near the analysis chamber. In this case, a protection device is needed (or even a cooled casing so as to get round the problem of temperature variations). The noise, which is superimposed on the diode laser signal and may be generated by the propagation of the signal, is eliminated, this being advantageous if it is desired to measure compositions having low concentrations of gaseous species.

Another advantage of the measurement system according to the invention is that it is unnecessary to remove the moisture from the gas sample before taking the measurement: it is therefore unnecessary, as in the systems of the prior art, to use a drying system. By reducing the optical path to a few tens of centimeters (1 to 100 cm, preferably 5 to 50 cm and ideally 10 to 15 cm) it is possible to achieve satisfactory signal transmission despite a high dust concentration. Filters are therefore unnecessary in the path of the sampled gas and the dead volume is therefore reduced.

Another advantage of the invention is that it is possible to vary the gas withdrawal rate from the off-gas duct. In conventional systems, too high a withdrawal rate saturates the filters and dryers. The use of a Venturi system and the absence of filters allow a higher withdrawal rate and therefore a shorter analysis response time.

An essential advantage of the invention is that in particular it allows the $CO_2$ concentration of the off-gas output by an electric furnace to be measured. According to the invention, means (cooled probe, line length, chamber, etc.) are provided that allow the gas temperature to be lowered down to less than 300° C., preferably down to 200° C. or below.

This allows the $CO_2$ content to be measured in addition to that of CO. Of course, it is also possible at this temperature to measure the concentration of other species, such as CO, $H_2O$, $O_2$ (and optionally the temperature of the gases, which would be of little interest here, given that it has been modified beforehand).

Preferably, the temperature of the gas in the analysis chamber is now only of the order of a hundred degrees (from around 20° C. to about 200° C. depending on the withdrawal rate). The shorter optical path also allows diode lasers of lower emitting power to be used.

The gas temperature is simply measured using a thermocouple. However, it is possible, as mentioned above, to use the measurements made on at least two $H_2O$ lines and to deduce the temperature therefrom by calculation (using an algorithm known per se). The temperature may thus be measured in real time, which allows the gas composition measurement to be refined.

It is possible with the system of the invention to measure the $CO_2$, CO, $H_2O$ and $O_2$ species simultaneously. The $CO_2$ concentration is measured at a temperature below 300° C., preferably between 20° C. and 200° C., using an absorption line at a wavelength different from that used for measuring the CO concentration. However, these two wavelengths may be achieved by the same laser source, the wavelength of which is modulated (using a TDL whose tunable wavelength can vary substantially over a wavelength range that is regularly scanned over the entire range thanks for example to a sawtooth control signal). The two wavelengths used are preferably located in the region of 1581 nm. These two absorption peaks possess the property of being relatively separate and of sufficient amplitudes. A simultaneous measurement of the CO and $CO_2$ content of the composition using the same equipment is therefore possible. To measure the oxygen and water content would require different equipment, since the wavelengths are too far from the usable wavelengths for CO and $CO_2$ (the scanned wavelength range is limited).

The abovementioned wavelengths were chosen so as to limit the interference between species according to the conventional composition of the off-gas in an electric arc furnace (in which CO (15–20% on average, peaks at more than 40%), $CO_2$ (20–25% on average), $H_2$ (10% on average), $H_2O$ (20% on average), $N_2$ and $O_2$ (variable amounts depending on the air intake) are present).

The following description of FIGS. 5, 6 and 7 relates more especially to the aspect of the invention concerned with the unclogging of the sampling probe 101.

The probe 101 takes a gas sample 112 into a region where the decomposition is representative of the atmosphere in the furnace. For example, in an electric arc furnace, the optimum region for taking the sample lies in the region called the gap 113, close to the center of the gas stream 112, undiluted by the incoming air 114, 115 before the bend 111 and before the cooled jacket 110. The combustible gases in the off-gas are, at this point, not yet burnt by the dilution air 114, 115.

To withstand the high temperature (around 1600° C. at least), the probe 101 is water-cooled, by water flowing in the cavity 102 placed concentrically around the region 106 through which the gases 112 in the probe 101 flow. Accretions of dust on the internal wall of the probe, which have to be removed, are shown at 103.

The moving mechanical part consists of a rod 105 fastened to which are one or more fins 104. This part 104, 105 is rotated by an air cylinder 124 so that the entire wall of the probe is cleaned by the passage of the fins (which in the case shown in FIG. 6 make a rotation of 180° about the axis 105). The fins are not necessarily continuous over the entire length of the rod.

Compressed air is injected at 125 and 126 at the top of the probe after or during the rotation of the fins so as to expel the dust accretions such as 103 that might adhere to the fins 104. The unclogging cycle may be repeated several times (a half-turn, or a quarter-turn on one side more than on the other side in the present example).

The gases from the probe are taken off via the orifice 123. A purge of compressed air or nitrogen may also be effected via this orifice. The cooling water circulates in the probe via the orifices 121 and 122.

The off-gas is taken off at 126 at the base of the probe (in FIG. 7) via the beveled opening 120, preferably directed countercurrently with respect to the gas 112.

The invention claimed is:

1. A method for measuring the quantity of chemical species contained in a high-temperature gas and especially the quantity of CO and/or $CO_2$ contained in a gas output by a metal treatment furnace, and especially an electric arc furnace (EAF) or a basic oxygen furnace (BOF) or converter, characterized in that a portion of the gas to be analyzed is taken off, its temperature is lowered down to less than 300° C. and then at least the quantity of CO and/or $CO_2$ present in this gas is measured by means of the coherent light signal that is emitted by a diode laser through said gas and recovered upon emerging from said gas wherein:

the gas to be analyzed is taken off by means of a probe of axial symmetry, characterized in that the probe includes a part that can move about the axis of symmetry of the probe and can remove the impurities that have built up on the internal wall of said probe by relative rotation of the part and/or of the probe about the axis; and additional pneumatic unclogging means using compressed air are provided.

2. The method of claim 1, characterized in that the concentration of other species in the high-temperature gas is also measured using a diode laser, and especially the concentration of at least one of the species chosen from CO and/or $O_2$ and/or $H_2O$ and/or $CO_2$.

3. The method of claim 1, characterized in that the temperature of the high-temperature gas is also measured using the diode laser.

4. The method of claim 1, characterized in that the diode laser is a tunable diode laser (TDL) is used whose wavelength is continually adjustable over a wavelength range.

5. The method of claim 1, characterized in that the wavelength range includes the 1581 nanometer wavelength.

6. A method for measuring the quantity of chemical species contained in a high-temperature gas and especially the quantity of CO and/or $CO_2$ contained in a gas output by a metal treatment furnace, and especially an electric arc furnace (EAF) or a basic oxygen furnace (BOF) or converter, characterized in that a portion of the gas to be analyzed is taken off, its temperature is lowered down to room temperature, and then at least the quantity of CO and/or $CO_2$ present in this gas is measured by means of the coherent light signal that is emitted by a diode laser through said gas and recovered upon emerging from said gas.

* * * * *